United States Patent
Smith et al.

(10) Patent No.: US 7,027,146 B1
(45) Date of Patent: Apr. 11, 2006

(54) METHODS FOR FORMING A CALIBRATION STANDARD AND CALIBRATION STANDARDS FOR INSPECTION SYSTEMS

(75) Inventors: Ian Smith, Los Gatos, CA (US); Christian Wolters, Campbell, CA (US); Yu Guan, San Jose, CA (US); Don Brayton, Sunland, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 219 days.

(21) Appl. No.: 10/185,308

(22) Filed: Jun. 27, 2002

(51) Int. Cl.
*G01N 21/88* (2006.01)

(52) U.S. Cl. .................................. 356/243.6

(58) Field of Classification Search ............. 356/243.4, 356/243.6
See application file for complete search history.

(56) References Cited

U.S. PATENT DOCUMENTS

| | | | | |
|---|---|---|---|---|
| 5,078,492 A | * | 1/1992 | Scheer | 356/243.1 |
| 5,402,082 A | * | 3/1995 | Eccleston et al. | 327/530 |
| 5,691,812 A | * | 11/1997 | Bates et al. | 356/243.4 |
| 5,804,460 A | * | 9/1998 | Bindell et al. | 438/16 |
| 6,016,194 A | * | 1/2000 | Girvin et al. | 356/337 |
| 6,091,493 A | | 7/2000 | Stover et al. | |
| 6,639,672 B1 | * | 10/2003 | Haavig et al. | 356/338 |

OTHER PUBLICATIONS

SEMI Draft Document 3094, "New Standard: Guide for Specifying Scanning Surface Inspection Systems for Silicon Wafers for the 130-nm Technology Generation," Jan. 2002, pp. 1-14.

SEMI Draft Document 3388, "New Standard: Practice for Calibrating Scanning Surface Inspection Systems using Certified Depositions on Monodisperse Polystyrene Latex Sphere on Unpatterened Semiconductor Wafer Surfaces," May 2002, pp. 1-10.

Sankaran et al., "Advanced Particle Sizing Technique for Development of High-Accuracy Scanner Calibration Standards," Oct. 1999, pp. 1-13.

Duke Scientific Corp., SURF-CAL™ Particle Deposition Standards, © 2002, 2 pages.

KLA-Tencor Corp., Surfscan $SP1^{DLS}$, © 2002, 4 pages.

National Institute of Standards & Technology, Certificate of Analysis, Standard Reference Material® 1963, Jan. 2001, 2 pages.

* cited by examiner

*Primary Examiner*—Richard A. Rosenberger
(74) *Attorney, Agent, or Firm*—Ann Marie Mewherter; Daffer McDaniel, LLP

(57) ABSTRACT

Methods for forming calibration standards for an inspection system and calibration standards are provided. One method includes scanning a first and a second specimen with an optical system. Master standard particles having a lateral dimension traceable to a national or international authority or first principles measurements are deposited on the first specimen. Product standard particles are deposited on the second specimen. In addition, the method includes determining a lateral dimension of the product standard particles by comparing data generated by scanning the two specimens. One calibration standard includes particles having a lateral dimension of less than about 100 nm deposited on a specimen. A distribution of the lateral dimension has a full width at half maximum of less than about 3%. The uncertainty of the lateral dimension is less than about 2%. Therefore, the standard meets the requirements for the 130 nm technology generation of semiconductor devices.

26 Claims, 4 Drawing Sheets

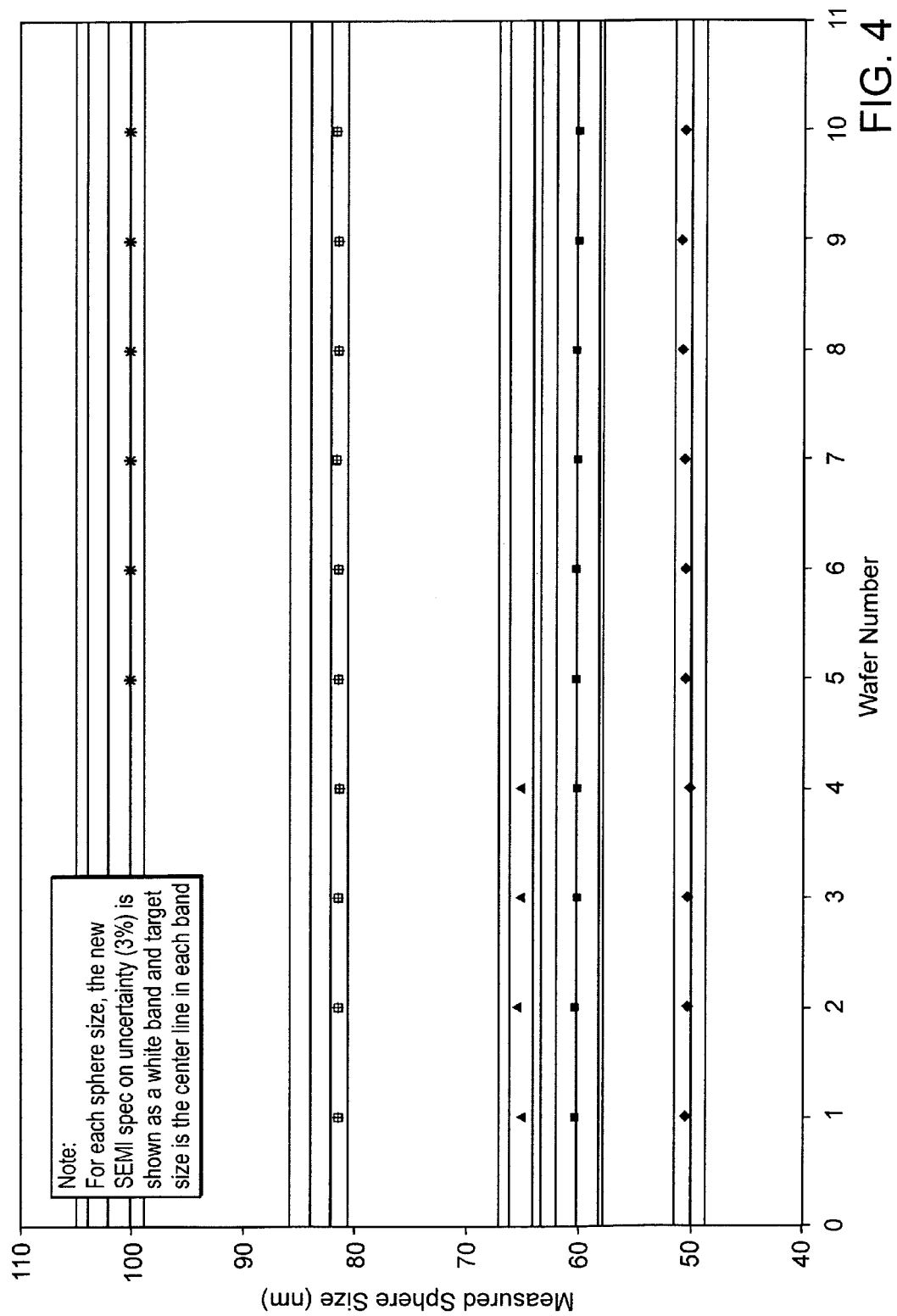

METHODS FOR FORMING A CALIBRATION STANDARD AND CALIBRATION STANDARDS FOR INSPECTION SYSTEMS

BACKGROUND OF THE INVENTION

1. Field of the Invention

This invention generally relates to methods for forming a calibration standard and calibration standards for inspection systems. Certain embodiments relate to calibration standards that include particles having a lateral dimension that is certified after deposition of the particles on a specimen.

2. Description of the Related Art

Monitoring and controlling semiconductor fabrication processes by inspection and metrology have become increasingly important in the successful fabrication of advanced semiconductor devices as the dimensions of semiconductor devices continue to shrink with advances in semiconductor materials and fabrication processes. For example, defects caused by particles on a surface of a wafer are responsible for a substantial portion of the yield loss of very large scale integrated circuits. Currently available systems that may be used for inspection include systems configured to detect particles or other defects on a specimen by light scattered from the specimen. In such systems, light illuminates the specimen at some incident angle. For a relatively smooth and flat surface, the light will reflect mostly specularly from the surface (i.e., the angle of reflected light equals the angle of incidence) and only a small portion of the incident light will be scattered away from the specular direction. If a defect is present, a larger portion of the incident light will be scattered away from the specular direction. Examples of defects that may be present on a specimen include, but are not limited to, particles, crystal-originated particles (COPs), surface roughness, ions, heavy metals, organic or inorganic layers, and subsurface imperfections.

Inspection systems are generally calibrated by measuring scatter from a standard source. A calibration standard may include polystyrene latex (PSL) spheres having a certified lateral dimension deposited on a specimen. Although PSL sphere contamination is generally not a problem in semiconductor manufacturing, PSL spheres were chosen as a scattering standard for inspection systems because of their spherical shape, well-known refractive index, and availability. PSL spheres are available in sizes typically ranging from tens of nanometers to tens of micrometers. The inspection system is calibrated using the measured response from a range of PSL sphere sizes that cover a portion of the range of the system. A relationship between detector response and PSL sphere diameter of sizes that were not calibrated may be produced by curve fitting, interpolation, or extrapolation of the data. Detector response can be converted into "PSL equivalent sizes." After the inspection system is calibrated, the inspection system can be used to inspect specimens having an unknown number and various types of defects on the specimens. When the inspection system is used to inspect a specimen, a relationship can be used to convert PSL equivalent information to a defect size. Such a relationship can be determined from scattering models for the defects of interest and the PSL spheres.

There are several problems with PSL spheres as a calibration standard. One problem is accurately determining the size of the spheres. For example, the size of PSL spheres reported by a manufacturer may be different than the size of the PSL spheres determined with a differential mobility analyzer (DMA) or light scattering. Changes in the size of the PSL spheres may produce a substantial change in scattered light. Therefore, scattered light is an extremely sensitive measurement for particle size, but accurate sizing of the PSL sphere used for calibration is also extremely important. In addition, the PSL size information is used to determine sizes of the defects. Therefore, the accuracy of the PSL size will affect the accuracy of the defect sizes determined by the inspection system. Variations in the refractive index of PSL spheres can also cause changes in scattering levels and substantial errors in determining particle sizes.

Furthermore, as the size of defects that are being inspected decreases, the size of the PSL spheres used for calibration standards should also decrease. In this manner, the inspection system is calibrated at approximately the size of the defects. In addition, the accuracy requirements of such standards increases. For example, Semiconductor Equipment and Materials International (SEMI) has proposed that for the 130 nm technology generation "to reduce PSL sphere sizing uncertainty in the 65 nm to 200 nm range, the diameter distribution should have a full width at half maximum (FWHM)$\leqq$5%. In addition, it is desirable that the peak PSL diameter as deposited on the wafer has an expanded uncertainty at 95% confidence level as small as possible but not greater than 3% (2$\sigma$)." ("SEMI Draft Document 3094 New Standard for Specifying Scanning Surface Inspection Systems for Silicon Wafers for the 130-nm Technology Generation," Jan. 21, 2002, page 13). However, currently available methods for producing a calibration standard for inspection systems can not meet the specification in terms of both size uncertainty and the ability to measure "as deposited on the wafer." In addition, as the size of PSL spheres decreases, the accuracy of the size decreases, and the size distribution increases thereby further complicating meeting the specification.

Accordingly, it would be advantageous to develop a method for forming a calibration standard that meets the proposed specification for at least the 130 nm technology generation described above and that has a PSL sphere size certified after deposition of the PSL spheres on a specimen.

SUMMARY OF THE INVENTION

An embodiment of the invention relates to a method for forming a calibration standard that may be used to calibrate inspection systems. The method may include scanning a first specimen with an optical system. Master standard particles having a lateral dimension traceable to a national or international authority or first principles measurements may be deposited on the first specimen. The method may also include depositing the master standard particles on the first specimen without filtering the master standard particles. The method may further include scanning a second specimen with the optical system. Product standard particles may be deposited on the second specimen. In addition, the method may include filtering the product standard particles to reduce a lateral dimension distribution of the product standard particles and to select product standard particles having approximately a predetermined lateral dimension and depositing the product standard particles on the second specimen. Furthermore, the method may include determining a lateral dimension of the product standard particles by comparing data generated by scanning the first specimen to data generated by scanning the second specimen.

In an additional embodiment, the method may also include depositing the master standard particles on the second specimen in addition to the product standard particles. For example, a method for forming a calibration standard for an inspection system may include scanning a specimen with an optical system subsequent to depositing master standard particles having a lateral dimension traceable to a national or international authority or first principle measurements on the specimen. The method may also include re-scanning the same specimen with the optical system subsequent to depositing product standard particles on the specimen. In addition, the method may include determining a lateral dimension of the product standard particles by comparing data generated by the two scans. The method may be further configured as described herein.

In one embodiment, the lateral dimension of the product standard particles may be less than about 100 nm. In another embodiment, the master standard particles and the product standard particles may be polystyrene latex spheres. In an additional embodiment, the lateral dimension of the master standard particles may be approximately equal to the lateral dimension of the product standard particles. Alternatively, the lateral dimension of the master standard particles may not be equal to the lateral dimension of the product standard particles. Therefore, determining the lateral dimension of the product standard particles may include interpolation.

As described herein, the lateral dimension of the product standard particles is determined after the particles have been deposited on a specimen. Therefore, in an embodiment, an uncertainty of the lateral dimension of the product standard particles due to variations in a parameter of a system used to deposit the product standard particles may be approximately 0%, or may be substantially eliminated. The sizing accuracy of deposition systems used to deposit particles may be reduced by variations in particle charge uniformity. Therefore, in an additional embodiment, an uncertainty of the lateral dimension of the product standard particles due to variations in particle charge uniformity may be approximately 0%, or may be substantially eliminated.

Furthermore, an uncertainty of the lateral dimension of the product standard particles due to differences between the system used to deposit the product standard particles and the optical system may be approximately 0%, or may be substantially eliminated. Such reduction, or even elimination, of uncertainty is advantageous because the optical system used to measure the calibration standard may have a configuration substantially equivalent to a configuration of an inspection system that will be calibrated with the standard. In contrast, the deposition system may have a substantially different configuration than the inspection system. The optical system may be a scanning scatterometry system. Scanning the first and second specimens may include detecting light scattered from the master standard particles and the product standard particles, respectively, at a substantially constant scatter angle. Therefore, an uncertainty of the lateral dimension of the product standard particles due to variations in a scatter angle of the optical system may be approximately 0%, or may be substantially eliminated.

Another embodiment relates to a method for certifying a calibration standard for an inspection system. The method may include calibrating an optical system with master standard particles deposited on a first specimen. A lateral dimension of the master standard particles may be traceable to a national or international testing authority or first principle measurements. The method may also include measuring a lateral dimension of product standard particles on a second specimen with the optical system. In addition, the method may include certifying the product standard particles on the second specimen as a calibration standard for an inspection system if the lateral dimension of the product standard particles is substantially equal to a predetermined lateral dimension. The predetermined lateral dimension may or may not be equal to the lateral dimension of the master standard particles. The method may include any other steps as described herein.

An additional embodiment relates to a calibration standard for an inspection system. The calibration standard includes particles deposited on a specimen. The lateral dimension of the particles may be less than about 100 nm. A distribution of the lateral dimension may have a full width at half maximum (FWHM) of less than about 3%. In addition, the uncertainty of the lateral dimension may be less than about 2%. Therefore, the calibration standard meets the proposed requirements for the 130 nm technology generation of semiconductor devices set out in "SEMI Draft Document 3094, New Standard: Guide for Specifying Scanning Surface Inspection Systems for Silicon Wafers for the 130-nm Technology Generation."

The lateral dimension of the particles may be certified by comparison to master standard particles having a lateral dimension traceable to a national or international authority or first principle measurements. An uncertainty of a lateral dimension of the particles due to variations in parameters of a system used to deposit the particles on the specimen may be approximately 0%, or may be substantially eliminated. The uncertainty of the lateral dimension due to differences between the system used to deposit the particles and the inspection system may be approximately 0%, or may be substantially eliminated. In addition, the uncertainty of the lateral dimension due to variations in a scatter angle of an optical system used to certify the calibration standard may be approximately 0%, or may be substantially eliminated. The lateral dimension may also be certified using an optical system having a configuration substantially equivalent to a configuration of the inspection system.

BRIEF DESCRIPTION OF THE DRAWINGS

Other objects and advantages of the invention will become apparent upon reading the following detailed description and upon reference to the accompanying drawings in which:

FIG. 4 depicts a plot of measured sphere size versus wafer illustrating the sizing accuracy of an embodiment of a method for forming a calibration standard for an inspection system.

Figure 1:
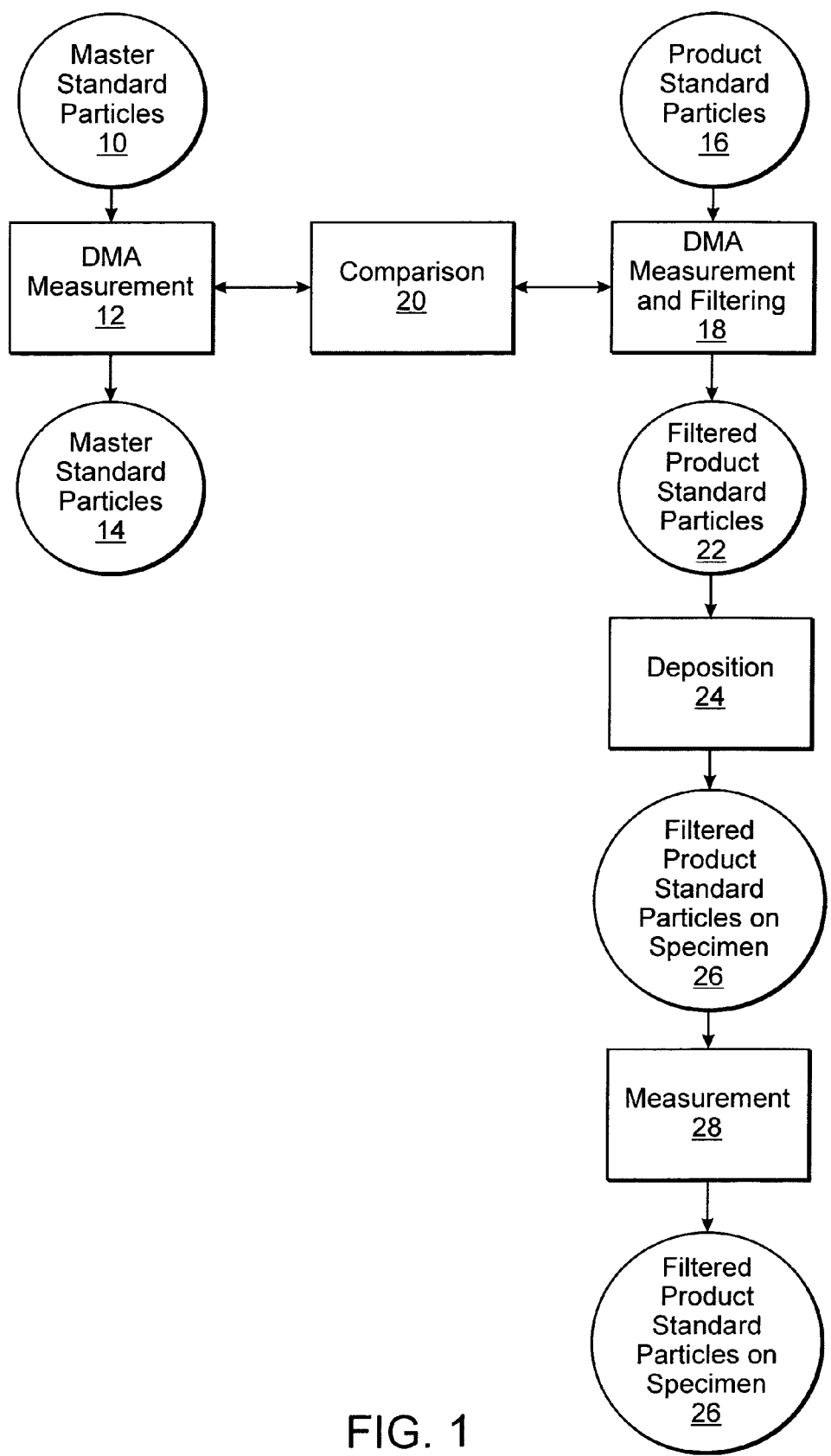
FIG. 1 depicts a flow chart illustrating a currently used method for forming a calibration standard for an inspection system.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, FIG. 1 illustrates a currently used method for forming a calibration standard. As shown in step 10, master standard particles such as polystyrene latex (PSL) spheres are obtained commercially and have a lateral dimension traceable to a national or international authority such as the National Institute of Standards and Technology (NIST). The lateral dimension of the master standard particles is measured with a differential mobility analyzer (DMA), as shown in step 12. After measurement, the master standard particles are in their original state such as an aerosol and are not deposited on a specimen, as shown in step 14.

As shown in step 16, product standard particles such as PSL spheres or "native PSL spheres" are obtained from a commercial source. As shown in step 18, the product standard particles are measured with a DMA and filtered to obtain the filtered product standard particles, as shown in step 22. The DMA measurement of the product standard particles is compared to the DMA measurement of the master standard particles, as shown in step 20. If the comparison of the DMA measurements indicates that the lateral dimension of the product standard particles equals the lateral dimension of the master standard particles, the product standard particles are certified as a calibration standard. After measurement and filtering, the product standard particles are deposited onto a specimen, as shown in step 24, to obtain the filtered product standard particles on the specimen, as shown in step 26. The specimen may include a product wafer that is to be used as a calibration standard. No further certification is done after the spheres are deposited on the specimen. The filtered product standard particles may be measured, as shown in step 28. The measurement may be performed using a scanning surface inspection system (SSIS). In this method, however, the SSIS measurement is not used to certify the calibration standard. The filtered product standard particles on the specimen, as shown in step 26 or step 30, are used as the calibration standard.

There are, however, several disadvantages to the method illustrated in FIG. 1. For example, PSL spheres having a lateral dimension of greater than about 100 nm can usually be deposited, either directly from an atomized aerosol or after filtering the aerosol through a DMA, without compromising their as-manufactured size distribution. Such deposition is possible because the lateral dimension distribution of such particles is sufficiently narrow to meet the proposed SEMI specification. The disadvantage to this method becomes more apparent as the sphere sizes decrease below approximately 100 nm where the lateral dimension distribution of the native spheres becomes broad with a less prominent peak. Consequently, it becomes more difficult for a DMA to accurately measure and filter the spheres, and the size uncertainty of deposited spheres may be larger than that permitted by the specification. For instance, the full width at half maximum (FWHM) size distribution of commercially available 83 nm spheres (commonly used for calibrating commercially available inspection systems) is from about 10% to about 15%. A DMA can be used to obtain a narrower distribution (to typically from about 5% to about 6%), but the uncertainty of the peak size will typically be from about 3% to about 5% ($2\sigma$). The uncertainty is even worse for smaller spheres. Therefore, this method fails to meet the proposed SEMI specification for the 130 nm technology generation in terms of both size uncertainty and the ability to measure "as deposited on the wafer." In addition, this method does not provide a means for detecting a sizing error made during deposition.

Figure 2:
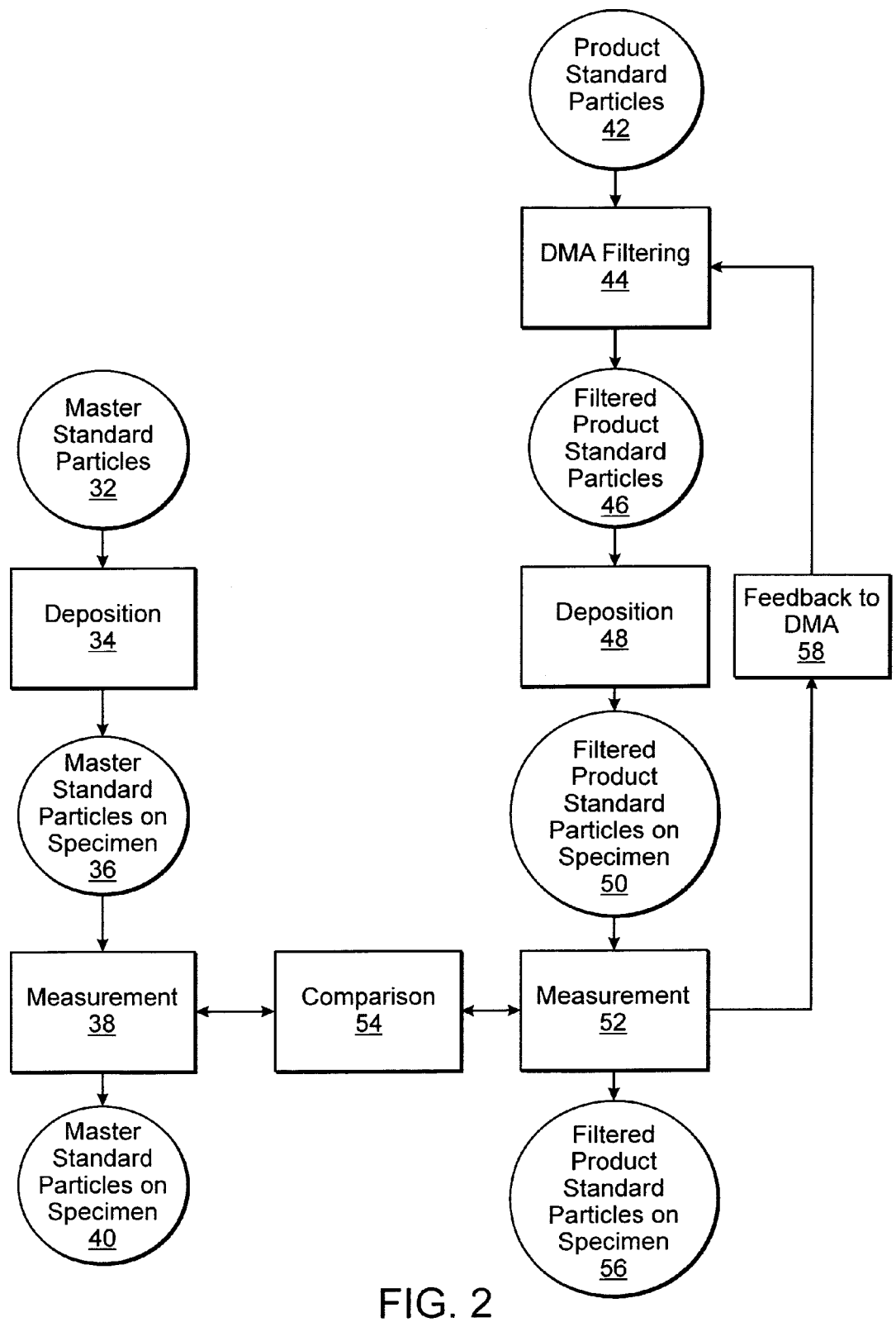
FIG. 2 depicts a flow chart illustrating an embodiment of a method for forming a calibration standard for an inspection system.

FIG. 2 illustrates an embodiment of a method for forming a calibration standard that meets the proposed SEMI specification for the 130 nm technology generation in terms of both size uncertainty and the ability to measure "as deposited on the wafer." As shown in step 32, master standard particles having a lateral dimension traceable to a national or international authority such as NIST are obtained. As used herein, the terms "national authority" and "international authority" are interchangeable for the methods and calibration standards described herein. For example, PSL spheres having manufacturer's size measurements and certification showing that the measurements are traceable to NIST may be used. PSL spheres may be obtained, for example, from Duke Scientific Corporation, Palo Alto, Calif. Alternatively, PSL spheres having lateral dimensions certified by NIST may be used. One example of master standard particles that are certified by NIST is Standard Reference Material® 1963. This Standard Reference Material consists of 5 mL of carboxylated PSL spheres in deionized (0.2 µm pore size filter) filtered water. The average particle size diameter is measured in air as an aerosol by electrical mobility measurements. The size distribution of the PSL spheres is narrow, with a standard deviation of 0.0018 µm excluding outliers. The number of undersized particles is negligible and the number of oversized particles (diameters greater than 0.2 µm) is less than 0.1%. The reported average particle size diameter, in µm, is 0.1007±0.0010. (National Institute of Standard & Technology, Certificate of Analysis, Standard Reference Material® 1963, Jan. 16, 2001, page 1). Alternatively, the master standard particles may have a lateral dimension traceable to first principle measurements. Any first principle measurements known in the art may be used to traceably measure the lateral dimension of the master standard particles. It is to be understood, however, that the master standard particles that can be used in this method are not limited to PSL spheres. For example, the master standard particles may also include, but are not limited to, silicon (Si), silicon dioxide ($SiO_2$), titanium (Ti), tungsten (W), copper (Cu), and any other material known in the art of integrated circuit manufacturing, magnetic recording media manufacturing, or reticle manufacturing.

As shown in step 34, the method includes depositing the master standard particles on a specimen. The specimen may be a semiconductor substrate such as a monocrystalline silicon substrate, which may be commonly referred to as a "wafer." The specimen, however, may also be any other appropriate specimen known in the art such as, but not limited to, a transparent substrate such as a glass substrate used for reticle manufacturing, magnetic recording media, or any other substrate. In addition, the specimen may include a substrate without any other layers formed on the substrate, which in the case of a silicon substrate is commonly referred to as a "bare wafer," or a substrate that has one or more layers formed on the substrate. The master standard spheres may be deposited directly (i.e., without being filtered) on a specimen, for example, by an atomized aerosol alone or by any other process known in the art. As shown in step 36, the master standard particles directly deposited on a specimen are used as a standard for product standard particles.

As shown in step 38, a lateral dimension of the master standard particles is measured by scanning the specimen with an optical system. In the case of PSL spheres, the lateral dimension that is measured is a diameter of the master standard particles. However, for non-spherical master standard particles, the lateral dimension may be a length or a width depending on the geometry of the master standard particles. As used herein, the term "lateral dimension" is equivalent to and is used interchangeably with the term "size." The optical system may be an SSIS. The system may be a scanning scatterometry system that has an illumination wavelength of about 488 nm. The illumination may be provided by a light source such as a laser. The illumination wavelength and the light source may vary, however, depending on, for example, the size of the particles and the material of the particles and the specimen. In addition, the illumination may include one or more wavelengths. One example of a commercially available SSIS is the Surfscan SP1 DLS available from KLA-Tencor Corporation, San Jose, Calif. The Surfscan SP1 DLS is a dual-laser system that uses multiple detectors. For inspection by scattered light, one laser captures defects by providing two modes of illumination: normal and oblique. In addition, the system has two channels for each mode of illumination. An appropriate channel or combination of channels in an SSIS, however, may vary depending upon, for example, defect sizing accuracy and sensitivity selected for the method. The optical system is configured to detect light scattered from the specimen and the particles at one or more substantially constant scatter angles. The same optical system may or may not be used throughout the method. In a preferred embodiment, the same optical system may be used throughout the method to reduce uncertainty that may be introduced if different systems are used.

Data generated from scanning the specimen may be available, obtained, and used in a number of ways. For example, if the optical system includes a number of channels, light detected with only one channel may be used to determine the lateral dimension of the particles. The channel that is selected should have adequate sensitivity to the lateral dimension of the particles. In general, however, signals from multiple channels can be used to improve the sizing accuracy assuming that the channels can detect particles having the lateral dimension of interest. The data may be used to generate a particle size histogram. For example, the system may use the raw data to determine the "mean" value or "modal" value of the particle sizes in the distribution. The modal value or "modal size" may be approximately equal to the mean value or the "mean size" of the particles if the size distribution is symmetrical. Although the methods are described herein with respect to the modal value or modal size, it is to be understood that the methods may also be performed with the mean value or any other quantitative measurement of the particle size distribution known in the art. There are many different ways that the modal value could be determined from the raw data (i.e., averaging, curve fitting, etc.), any of which can be used for the method if the particle sizing is within the limits for the method. The modal value of the particle sizes measured by the optical system should be recorded. Alternatively, the optical system may be calibrated with the master standard particles such that the data generated by the optical system yields a modal particle size approximately equal to that of the lateral dimension of the master standard particles. This data may be compared to measurements of product standard particles deposited on other specimen as described herein. The master standard particles on the specimen, as shown in step 40, may be stored appropriately such that the master standard particles may be reused at a later time.

As shown in step 42, product standard particles may be obtained from a commercial source. Examples of commercial sources of product standard particles include, but are not limited to, Duke Scientific and JSR Corporation, Tokyo, Japan. The product standard particles may include PSL spheres or any other particles as described above. The product standard particles may have a lateral dimension of less than about 100 nm. The lateral dimension, however, may vary depending on, for example, the particles that are available and the size of defects being detected by an inspection system to be calibrated with the standard. For example, the product standard particles may have a lateral dimension of about 20 nm, about 30 nm, about 50 nm, about 60 nm, about 83 nm, about 102 nm, about 126 nm, about 155 nm, about 204 nm, and about 304 nm.

As shown in step 44, the product standard particles may be filtered using a DMA. A DMA generally operates by having charged particles flowing in an air stream drawn sideways toward a charged hollow rod with a narrow slit in it. The deviation induced in a particle path by the electric field varies with air resistance, which depends on particle diameter. As a result, only a narrow range of particle diameters are able to pass through the slit. By controlling airflow rate, voltage, and system geometry, particle sizes can be determined. DMA's are commercially available from TSI Incorporated, Shoreview, Minn. and MSP Corporation, Minneapolis, Minn. Filtering the product standard particles may reduce a lateral dimension distribution of the product standard particles. For example, the lateral distribution of the product standard particles may be reduced from about 10% to about 15% before filtering to from about 3% to about 5% after filtering for 83 nm diameter PSL spheres.

Filtering may also be used to select product standard particles having approximately a predetermined lateral dimension. For example, typical commercially available PSL spheres having an average lateral dimension of about 50 nm may be filtered to obtain PSL spheres having a lateral dimension anywhere in a range of about 30 nm to about 65 nm with a relatively narrow distribution. The predetermined lateral dimension may or may not be equal to a lateral dimension of the master standard particles. The predetermined lateral dimension should be within a range of particle sizes to be detected by an inspection system. In this manner, an inspection system may be calibrated within a range of defect sizes to be detected by the inspection system with a calibration standard as described herein. The filtered product standard particles, as shown in step 46, may have an acceptable lateral dimension distribution and a lateral dimension approximately equal to a predetermined lateral dimension. However, the filtered product standard particles may not have an acceptable lateral dimension distribution and the predetermined lateral dimension, which is determined in the following steps, and one or more parameters of the DMA may have to be adjusted as described herein. Throughout the entire process illustrated in FIG. 2, the DMA is only used as a particle size selection tool and not as a metrology tool. All particle size measurements are performed using the optical system as described herein.

As shown in step 48, the filtered product standard particles may be deposited on a specimen, which may or may not be used only in the process of finding the correct particle size through the iterations shown in step 58 and may or may not be the same specimen used for the final calibration standard product. The specimen may include a semiconductor wafer or any other specimen as described above. Preferably, the product standard particles and the master standard particles are deposited on specimens that are formed of substantially the same material and that have substantially equivalent surface characteristics. In this manner, light scattered by the two specimens that is not attributable to the particles may be substantially the same. In an alternative embodiment, the product standard particles and the master standard particles may be deposited on the same specimen. As such, uncertainty caused by light scattered by the specimen that is not attributable to the particles may be substantially eliminated. Therefore, in one embodiment, the method shown in FIG. 2 can be modified to include scanning a specimen with an optical system subsequent to depositing master standard particles having a lateral dimension traceable to a national or international authority on the specimen and re-scanning the same specimen with the optical system subsequent to depositing product standard particles on the specimen. In addition, the method may include determining a lateral dimension of the product standard particles by comparing data generated by the two scans as described herein. The filtered product standard particles on the specimen, as shown in step 50; may be processed through the following certification steps.

As shown in step 52, the filtered product standard particles are measured by scanning the specimen with the same optical system that was used in step 38. Alternatively, the filtered product standard particles may be measured by scanning the specimen with a different optical system than that used in step 38. Scanning the specimen may be performed by detecting light scattered from the specimen and the product standard particles at a substantially constant scatter angle. Data generated from scanning the specimen may be available, obtained, and used in a number of ways as described above. As shown in step 54, the method includes determining a lateral dimension of the product standard particles by comparing the data generated by scanning the specimen on which master standard particles are deposited to the data generated by scanning the specimen on which product standard particles are deposited. For example, the modal size of spheres or any other type of data generated from both scans may be compared. If the modal sizes are substantially the same, then the filtered product standard particles on the specimen, as shown in step 56, may be certified as a calibration standard. In this example, the calibration standard is certified as having product standard particles that have a lateral dimension substantially equal to a lateral dimension of the master standard particles. Therefore, the method provides traceable size measurements of the particles as deposited on a specimen thereby meeting the SEMI specification, and in particular the requirement that the peak PSL diameter as deposited on the wafer is measured. In addition, unlike the method shown in FIG. 1, the SSIS is used in the chain of traceability to NIST standards or master standard particles having a lateral dimension traceable to first principle measurements.

In an alternative embodiment, the size of the product standard particles does not have to match the size of master standard, or NIST certified or first principles measured, particles. For example, the size of the product standard particles may be determined using an SSIS measurement through interpolation if the size is close to one or more available master standard, or NIST certified or first principles measured, particle sizes. Alternatively, the SSIS used in steps 38 and 52 may be newly calibrated with master standard, or NIST certified or first principles measured, particles in the applicable range.

In addition, if the modal sizes are not substantially the same, the displacement between the modal sizes may be calculated. The displacement may be used to alter one or more parameters of the DMA filtering step using a feedback control technique, as shown in step 58. For example, the voltage and/or the airflow rate of the DMA may be altered such that product standard particles subsequently deposited on other specimens may have a modal size closer, or preferably equal, to the modal size of the master standard particles. In this manner, any perturbations in the product standard particle sizing caused by the DMA during deposition can be detected and corrected. The above feedback loop may be repeated for each subsequent deposition of product standard particles until the product standard particles have a lateral dimension substantially equivalent to the predetermined lateral dimension and an acceptable lateral dimension distribution. After this process is completed, the product standard particles may be deposited on a new specimen rather than the one used during the size selection process. In addition, because the method includes a feedback loop to alter the DMA filtering, the DMA filtering may be controlled to any degree depending on the lateral dimension and lateral dimension distribution requirements for a calibration standard. Such a feedback loop may be particularly useful as the lateral dimension of particles for calibration standards decreases, and the lateral dimension distribution of commercially available particles increases.

The method shown in FIG. 2 can be used to re-establish NIST standard traceability, traceability to other standards, or traceability to first principles measurements of the measurement of product standard particles such as PSL spheres after the spheres are deposited on specimens such as wafers and to ensure that the SSIS calibration standards meet the forthcoming proposed SEMI specification for calibration standards for particle inspection. As shown in FIG. 2, the method provides the most direct tracing path to NIST's size standard or first principles measurements. In addition, the uncertainty is only affects by the precision of the optical system because size certification of the deposited spheres is measured directly with an optical system such as an SSIS. Therefore, an uncertainty of the lateral dimension due to variations in parameters of a system used to deposit the product standard particles is approximately 0%, or may be substantially eliminated. In comparison, to trace an optical system measurement to a NIST standard in the currently used method shown in FIG. 1, the tracing path is through the optical system calibration, the particle deposition system, and the DMA calibration. Any errors and variations (i.e., flows, pressure, temperature on the DMA based deposition system, which are subject to changes) in any of these stages contribute to the sizing uncertainty. As such, lateral dimensions of particles certified with the currently used method are subject to uncertainty caused by variations in the system used to deposit the particles.

There are several additional advantages to the method illustrated in FIG. 2. One advantage is that an optical system such as an SSIS is typically more precise than a DMA for measuring particle sizes. For example, an SSIS determines the particle size by measuring the amount of scattered light, which in the situation discussed herein (i.e., particle sizes of about 65 nm to about 200 nm and an illumination wavelength of about 488 nm) is generally proportional to about the sixth power of the particle size. This approximation is for this example only and will increase with particle size. With a DMA, the particle size is determined by measuring the applied voltage, which is about linearly proportional to the particle size. In this manner, an SSIS measurement is about six times more sensitive to relative particle size changes than a DMA measurement. Table 1 illustrates approximate numerical results of a comparison between DMA and SSIS measurements of 83 nm spheres, which may be obtained from Duke Scientific.

TABLE 1

|  | Native Spheres | DMA (10:1) ratio | DMA (20:1) ratio | SSIS (SP1-DLS) | SEMI spec |
|---|---|---|---|---|---|
| Availability/effective status | Current | Current | Near Future | Current | Near Future |
| FWHM Distribution (%) | 10–15 | 5 | 2.5 | 0.6 | 5 |
| Size measurement uncertainty (%) | N/A | 3–5 | 2–3 | 0.5–1 | 3 |

The ratios for the DMA refer to the sheath to aerosol flow ratio used on a DMA and the values shown here are those practical for DMA based systems. The FWHM values for the metrology tools (DMA or SSIS) are theoretical variations in measured values for perfectly monodisperse spheres reflecting the precision of the tools. The measurement uncertainties are $2\sigma$ sizing errors based on experiments, which largely depend on the precision, but are also affected by other particle factors such as the size distribution of the particles. The FWHM distribution and the uncertainty will vary depending on the size of the particles. As shown in Table 1, a DMA with a 20 to 1 flow ratio should be sufficient to produce a size distribution that meets the SEMI specification, but is marginal in terms of size uncertainty. Therefore, the comparison between a DMA and an SSIS shows that only an SSIS can meet the SEMI uncertainty requirement with high confidence.

As described above, therefore, the method shown in FIG. 2 provides calibration standards that meet the proposed SEMI specification requiring a relatively small size uncertainty and relatively narrow size distribution to be used for surface contamination inspection. For example, as further described above, an SSIS is more accurate than a DMA for the methods described herein. Therefore, the method may be used to provide higher accuracy calibration standards, and in particular for PSL spheres with a broad native size distribution. Such broad size distributions are particularly problematic for sphere sizes below about 100 nm. For example, the spheres must be filtered to reduce the size distribution. Therefore, in the method shown in FIG. 1, the traceability would be lost after such spheres are filtered by the DMA. In addition, the method shown in FIG. 2 may be used to consistently meet the proposed SEMI specification for size uncertainty of PSL spheres below 100 nm, which is not possible with traditional DMA metrology. Furthermore, because the lateral dimension of the PSL spheres is determined with greater accuracy than with traditional DMA metrology, the inspection systems calibrated with such calibration standards may also determine a lateral dimension of defects with greater accuracy.

An additional advantage of the method illustrated in FIG. 2 is that the measurement technique is substantially the same as that used in the majority of product applications (i.e., laser light scatterometry). Therefore, systematic errors caused by inconsistencies between SSIS measurements and DMA measurements can be avoided. For instance, particle charge uniformity and shape may affect DMA measurement results by variations in mobility and aerodynamic drag. Such variations, however, would have either little effect on an SSIS measurement or affect it in a different way. In this manner, an uncertainty of the lateral dimension of the product standard particles due to differences between the system used to deposit the product standard particles and the inspection system is approximately 0%, or may be substantially eliminated. In addition, an uncertainty of the lateral dimension of the product standard particles due to variations in particle charge uniformity is approximately 0%, or may be substantially eliminated.

A further advantage of the method illustrated in FIG. 2 is that the method can be used to re-certify calibration standards. In this manner, calibration standard life may be extended. In addition, the overall cost of calibration standards may be reduced, and a baseline shift in inspection data due to the introduction of new calibration standards may be avoided. The method also provides continuity between traditional PSL deposited calibration standards, absolute contamination standards (ACS), and new calibration standards. The traditional calibration standards include PSL spheres having a lateral dimension greater than about 100 nm and certified as traceable to NIST when the manufacturer's measurements provide such traceability. The new calibration standards (produced with the method illustrated in FIG. 2 in which NIST traceability or first principles measurements traceability is re-established after deposition) include PSL spheres having a lateral dimension less than about 100 nm where the effect of the DMA is strong enough to void the manufacturer's traceability during deposition.

An additional advantage of the method illustrated in FIG. 2 is that the method includes scanning the specimens at a substantially constant scatter angle. In this manner, an uncertainty of the lateral dimension of the product standard particles due to variations in a scatter angle of the optical system is approximately 0%, or may be substantially eliminated. In contrast, another method known in the art involves detecting scattered light from a surface as a detector moves through a continuous range of scatter angles from negative scatter angles, through 0 at surface normal, and then through positive scatter angles. This technique is commonly referred to as complete angle-resolved scattering instrument (CASI) scanning, and one example of such a method is illustrated in U.S. Pat. No. 6,091,493 to Stover et al., which is incorporated by reference as if fully set forth herein. The method is also described by Sankaran et al., in "Advanced Particle Sizing Technique for Development of High-Accuracy Scanner Calibration Standards," Technology Transfer # 99083800B-TR, Oct. 8, 1999, SEMATECH, Inc., Austin, Tex. Therefore, although this method uses an optical technique, the CASI technique is substantially different than the optical technique described herein. In addition, variations and/or uncertainties of the scatter angle will contribute to the uncertainty of the lateral dimension of the particles. Furthermore, due to the number of scatter angles at which scattered light is detected, measurements taken with this method take a much longer time than the measurements described herein.

The CASI method also uses a model for determining the particle size directly from the scattered light signal as a function of scatter angle. The model calculates scatter from particles on a perfectly smooth surface to determine a lateral dimension of the particles. Effects from surface roughness, and other sources of non-particle scatter, are not included in the model. The model presents scatter data in units of differential scattering cross-section, which is the scattered light per unit solid angle divided by the incident intensity at the particle. In contrast, the method described herein involves determining particle sizes indirectly by comparing data of particles being certified to data from known masters (i.e., master standard particles having a traceably measured lateral dimension). The comparison of data that is used as described herein to certify the lateral dimension of the particles is a much simpler and more straightforward technique. In addition, the methods described herein may have negligible error caused by scattered light from sources other than the particles if the specimens on which the master standard particles and the product standard particles are the same or if the effect of the specimens on the response is known.

In addition, there are differences between a CASI scanning system and inspection systems commonly used in product applications and calibrated with the calibration standards. For example, such inspection systems generally do not involve detecting scattered light throughout a range of scatter angles. Therefore, there may be systematic differences caused by inconsistencies between CASI measurements and SSIS measurements, which can increase the uncertainty of the lateral dimension of the particles. Such systematic differences and uncertainty can be avoided by using the method illustrated in FIG. 2.

Figure 3:
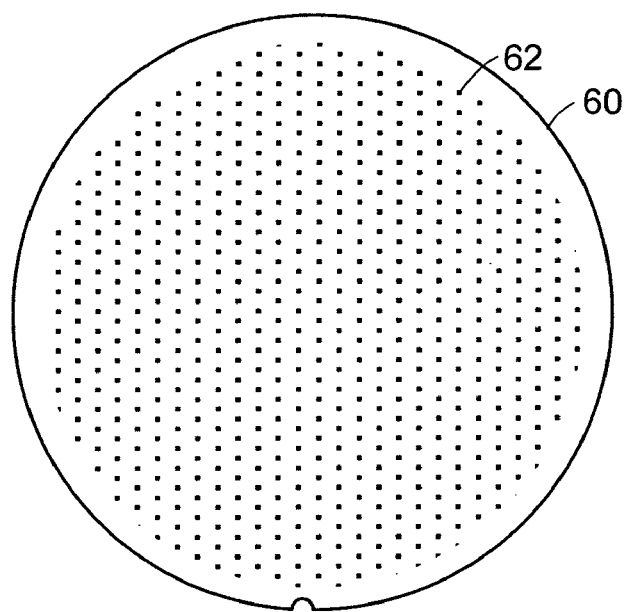
FIG. 3 depicts top schematic views of various embodiments of a calibration standard for an inspection system.
Figure 3:
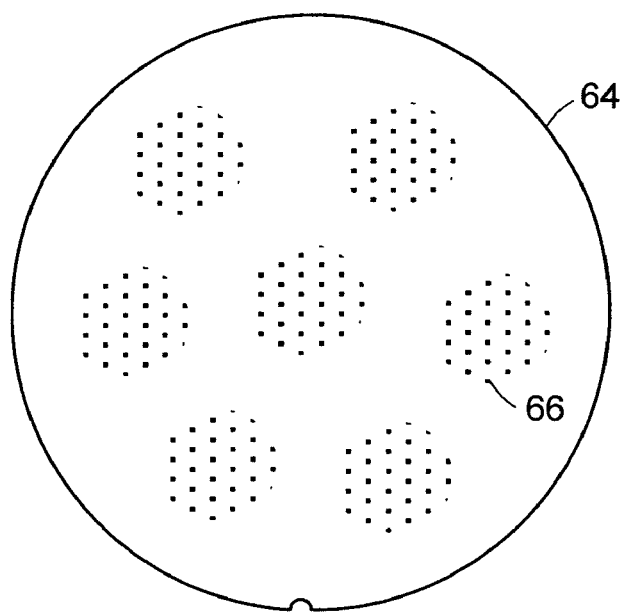

FIG. 3 illustrates various embodiments of a calibration standard for an inspection system that may be formed by the method illustrated in FIG. 2. Calibration standard 60 is a semiconductor wafer. PSL spheres 62 are deposited on approximately an entire surface area of the wafer in a full wafer deposition. A substantial portion of PSL spheres 62 may have approximately the same lateral dimension. Alternatively, PSL spheres 62 may have a number of different lateral dimensions. The number of particles that are deposited on calibration standard 60 may range from about 500 particles to about 30000 particles depending on the size of the standard.

Calibration standard 64 is also a semiconductor wafer. PSL spheres 66 are deposited in multiple spots on the surface of the wafer in spot depositions. PSL spheres 66 in each spot may have approximately the same lateral dimension. Alternatively, PSL spheres 66 in different spots may have one or more different lateral dimensions. A diameter of the spots may range from about 10 mm to about 100 mm, and the number of particles in each spot may range from about 100 particles to about 7000 particles. The size of the spots and the number of particles per spot may vary depending on the size of the calibration standard. The number of spots per standard may also vary from about 2 spots per standard to about 50 spots per standard depending on the lateral dimensions of the specimen. In addition, the spots may be located on the specimen in any arrangement. A calibration standard that includes multiple spot depositions of particles may reduce the time involved in calibrating an inspection system and may reduce the costs associated with multiple calibration standards. In an additional embodiment, a calibration standard may include particles deposited on the specimen in any other arrangement known in the art such as a half wafer deposition. Calibration of an inspection system using calibration standard 60 or calibration standard 64 may be performed by counting the number of spheres vs. sphere size.

In alternative embodiments, a calibration standard may include any substrate known in the art. The calibration standard may also include substrates of different sizes and shapes such as semiconductor wafers, which are substantially round as shown in FIG. 3, having a diameter of about 150 mm, about 200 mm, or about 300 mm and transparent substrates suitable for reticle manufacturing, which may be square and may have lateral dimensions of about 5 inches by about 5 inches, or about 6 inches by about 6 inches. In addition, calibration standards 60 and 64 may include other particles deposited upon a specimen as described above instead of or in addition to PSL spheres. For example, calibration standards 60 and 64 may also include master standard particles deposited upon a specimen in addition to product standard particles. The particles may also include spherical particles and/or particles having other shapes. The particles may have a lateral dimension of less than about 100 nm. In a further alternative embodiment, the calibration standard may include subsurface defects instead of surface defects. Examples of subsurface defects may include pits or other features formed into the specimen and below the upper surface of the specimen. Such subsurface defects may be formed using any process known in the art such as masking and etching the specimen.

A calibration standard formed by the method illustrated in FIG. 2 provides several advantages over other calibration standards. For example, an uncertainty of a lateral dimension of the particles due to variations in parameters of a system used to deposit the particles on the specimen is approximately 0%, or may be substantially eliminated, because the particles are traceably measured after the particles are deposited on the specimen. In addition, a distribution of the lateral dimension may have a FWHM of less than about 3% because the distribution of the lateral dimension is reduced by filtering, which may or may not be controlled with a feedback loop as described above. Furthermore, the uncertainty of the lateral dimension is less than about 2%. This uncertainty is lower than that achievable by the method illustrated in FIG. 1 at least because the SSIS measurement is more accurate than a DMA measurement.

An additional advantage of a calibration method formed by the method illustrated in FIG. 2 is that the lateral dimension of the product standard particles is certified by comparison to master standard particles having a lateral dimension traceable to a national or international authority or first principles measurements. As described above, the comparison of SSIS measurements is used to certify the lateral dimension of the particles thereby providing a more direct traceable path than other methods for forming a calibration standard. The uncertainty of the lateral dimension due to variations in a scatter angle of an optical system used to certify the calibration standard is approximately 0%, or may be substantially eliminated, because the optical system used to certify the calibration standard has a substantially constant scatter angle. In addition, the uncertainty of the lateral dimension due to differences between the system used to deposit the particles and the inspection system to be calibrated with the calibration standard is approximately 0%, or may be substantially eliminated, because the method illustrated in FIG. 2 avoids any systematic errors caused by inconsistencies between SSIS and DMA lateral dimension measurements. Furthermore, the lateral dimension is certified using an optical system having a configuration substantially equivalent to a configuration of the inspection system to be calibrated with the calibration standard. For example, the optical system used in the method illustrated in FIG. 2 and the inspection system may be laser light scatterometry systems.

EXAMPLE

Sizing Accuracy

FIG. 4 is a plot of measured PSL sphere size versus wafer illustrating the sizing accuracy of an embodiment of a method for forming a calibration standard for an inspection system. The method that was used to generate the data in FIG. 4 is included here for example purposes only. The method illustrated in FIG. 2 may or may not include the following steps. A SurfScan SP1 DLS was selected to be calibrated and used for the entire process of forming the calibration standards (i.e., pre-scans, mid-scans, and post-scans). If the process is interrupted by other work or by an interval of time of more than one day, the calibration may or may not be repeated. To calibrate the SurfScan SP1 DLS, calibration wafers made with full wafer, direct (without DMA filtering) depositions of 60 nm and 83 nm PSL spheres were placed in a cassette. The two calibration wafers were scanned with oblique illumination, and scattered light was collected with a dark field, wide scatter angle channel. The peak intensity, in raw ppm, was recorded. These values were entered in a normalization curve in a calibration algorithm.

A wafer was pre-scanned on the SurfScan SP1 DLS, calibrated as described above, with oblique illumination, and scattered light was collected with a dark field, wide scatter angle channel in a low throughput mode.

A mixture of PSL spheres was selected or was prepared using the following steps. DI water was run at a moderate flow rate for about 2 minutes, and then the flow rate was reduced to a flow rate appropriate for filling bottles. Aqueous suspensions of the PSL spheres were diluted with the DI water depending on sphere size. For example, 5 µl of 50 nm spheres was diluted in 100 ml of DI water, 5 µl of 60 nm spheres was diluted in 60 ml of DI water, 5 µl of 65 nm spheres was diluted in 30 ml of DI water, and 5 µl of 83 nm spheres was diluted in 30 ml of DI water. The bottles were rinsed prior to filling with the diluted suspensions.

A DMA available from MSP Corporation was used for the method. An atomizer with a small baffle was used. The atomizer, the o-ring, and the bowl were rinsed, wiped with a clean wipe, rinsed, and ultrasonicated for at least 5 minutes. All components were then rinsed, and the water was allowed to drain. The o-ring was placed in the groove at the top of the bowl.

A sphere mixture was then selected for deposition. About $3/16$ inch to about $1/2$ inch (about 15 ml to about 40 ml) of the sphere mixture was placed in the bowl, and the o-ring and atomizer was installed. The number of particles selected for deposition was 1000. The nozzle height was set to 11.5 mm gage. The nozzle was set to inner nozzle for 8 inch wafers and outer nozzle for 12 inch wafers. The DMA was initialized, and the DMA voltage and the condensation particle counter (CPC) reading were recorded. A "dummy deposition" was performed, and the CPC was recorded. The deposition time and the first accumulated count interval were calculated. A wafer was placed on the stage, and the notch was aligned. The deposition was started. The starting CPC reading, the estimated time for deposition, and the first interval of the deposition count were recorded. The wafer was removed on completion of the deposition.

The wafer was scanned on the SurfScan SP1 DLS with the same process used above. The results of the deposition were compared to specified characteristics for the wafer. Any necessary adjustments were made to the deposition process, and the deposition was completed on this wafer. If the wafer was out of specification and could not be brought into specification with subsequent depositions, the discrepancy was noted, and the process was continued to complete the wafer for use as a test vehicle for the remaining product calibration wafers. Another wafer would be selected and processed according to the above steps to replace the wafer, which is out of specification.

The following characteristics and corresponding adjustments, if necessary, were made. For example, the location of the spheres was compared to the selected location on the wafer. The position of the wafer on the stage can be altered to correct a spot dislocation. The 1000 count target should deposit between 200 and 600 particles to enable identification of the modal size. If the modal size is off by more than about 0.5 nm, another deposition process can be selected containing a higher or lower sphere size to bring the deposited sphere size into specification. If the size of a spot deposition is unacceptable, the DPC voltage can be increased to decrease spot size or can be decreased to increase spot size. The particle count is compared to count specifications, and a subsequent deposition target count can be determined to increase the number of particles on the wafer to meet the specification. Depositions of the same particle size on subsequent wafers can be completed with the adjusted parameters. The target count for subsequent depositions can be raised by 1000. The wafers were then scanned with the SurfScan SP1 DLS and packaged according to clean room specification.

As shown in FIG. 4, the above process was repeated to form a number of wafers for sphere sizes of about 50 nm, about 60 nm, about 65 nm, about 83 nm, and about 100 nm. The measured sphere size, in units of nm, was plotted versus wafer number. For each sphere size, the proposed SEMI specification for uncertainty (3%) is shown as a white band, and the target size is the center line in each band. Each deposition that was made falls within the SEMI specification for uncertainty. Therefore, the above process can be used to produce calibration standards that meet the proposed SEMI specifications for the 130 nm technology generation.

It will be appreciated to those skilled in the art having the benefit of this disclosure that this invention is believed to provide methods for forming calibration standards and calibration standards for inspection systems. Further modifications and alternative embodiments of various aspects of the invention will be apparent to those skilled in the art in view of this description. For example, the methods described herein can be used for other particles and in areas other than the microelectronics industry such as sizing of bio-molecules and organic growth clusters. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for forming a calibration standard for an inspection system, comprising:
    scanning a first specimen with an optical system, wherein master standard particles having a traceable lateral dimension are deposited on the first specimen;
    scanning a second specimen with the optical system, wherein product standard particles are deposited on the second specimen; and
    determining a lateral dimension of the product standard particles by comparing data generated by said scanning the first specimen to data generated by said scanning the second specimen.

2. The method of claim 1, wherein the lateral dimension of the master standard particles is traceable to a national or international authority.

3. The method of claim 1, wherein the lateral dimension of the master standard particles is traceable to first principles measurements.

4. The method of claim 1, wherein the lateral dimension of the product standard particles is less than about 100 nm.

5. The method of claim 1, wherein the master standard particles and the product standard particles comprise polystyrene latex spheres.

6. The method of claim 1, further comprising depositing the master standard particles on the first specimen without filtering the master standard particles.

7. The method of claim 1, further comprising filtering the product standard particles to reduce a lateral dimension distribution of the product standard particles and to select product standard particles having approximately a predetermined lateral dimension and depositing the product standard particles on the second specimen.

8. The method of claim 1, wherein an uncertainty of the lateral dimension of the product standard particles due to variations in parameters of a system used to deposit the product standard particles is substantially eliminated.

9. The method of claim 1, wherein an uncertainty of the lateral dimension of the product standard particles due to variations in particle charge uniformity is substantially eliminated.

10. The method of claim 1, wherein an uncertainty of the lateral dimension of the product standard particles due to differences between the system used to deposit the product standard particles and the inspection system is substantially eliminated.

11. The method of claim 1, wherein the optical system comprises a scanning scatterometry system.

12. The method of claim 1 wherein said scanning the first specimen and said scanning the second specimen comprise detecting light scattered from the master standard particles and the product standard particles, respectively, at a substantially constant scatter angle.

13. The method of claim 1, wherein an uncertainty of the lateral dimension of the product standard particles due to variations in a scatter angle of the optical system is substantially eliminated.

14. The method of claim 1, wherein the lateral dimension of the master standard particles is approximately equal to the lateral dimension of the product standard particles.

15. The method of claim 1, wherein the lateral dimension of the roaster standard particles is not equal to the lateral dimension of the product standard particles, and wherein said determining further comprises interpolation.

16. A method for certifying a calibration standard for an inspection system, comprising;
calibrating an optical system with master standard particles deposited on a first specimen, wherein the master standard particles have a traceable lateral dimension;
measuring a lateral dimension of product standard particles on a second specimen with the optical system; and
certifying the product standard particles on the second specimen as a calibration standard for an inspection system if the lateral dimension of the product standard particles is substantially equal to a predetermined lateral dimension.

17. A calibration standard for an inspection system, comprising particles deposited on a specimen, wherein an uncertainty of a lateral dimension of the particles due to variations in parameters of a system used to deposit the particles on the specimen is substantially eliminated, and wherein the lateral dimension is certified by comparison to master standard particles having a traceable lateral dimension.

18. The standard of claim 17, wherein the lateral dimension of the particles is less than about 100 nm.

19. The standard of claim 17, wherein a distribution of the lateral dimension of the particles has a full width at half maximum of less than about 3%.

20. The standard of claim 17, wherein the uncertainty of the lateral dimension of the particles is less than about 2%.

21. The standard of claim 17, wherein the lateral dimension of the master standard particles is traceable to a national authority.

22. The standard of claim 17, wherein the lateral dimension of the master standard particles is traceable to first principles measurements.

23. The standard of claim 17, wherein the uncertainty of the lateral dimension of the particles due to differences between the system used to deposit the particles and the inspection system is substantially eliminated.

24. The standard of claim 17, wherein the uncertainty of the lateral dimension of the particles due to variations in a scatter angle of an optical system used to certify the calibration standard is substantially eliminated.

25. The standard of claim 17, wherein the lateral dimension of particles is certified timing an optical system having a configuration substantially equivalent to a configuration of the inspection system.

26. A method for forming a calibration standard for an inspection system, comprising:
scanning a specimen with an optical system subsequent to depositing master standard particles having a traceable lateral dimension on the specimen;
re-scanning the specimen with the optical system subsequent to depositing product standard particles on the specimen; and
determining a lateral dimension of the product standard particles by comparing data generated by said scanning to data generated by said re-scanning.

* * * * *

UNITED STATES PATENT AND TRADEMARK OFFICE
CERTIFICATE OF CORRECTION

| | | |
|---|---|---|
| PATENT NO. | : 7,027,146 B1 | Page 1 of 1 |
| APPLICATION NO. | : 10/185308 | |
| DATED | : April 11, 2006 | |
| INVENTOR(S) | : Smith et al. | |

It is certified that error appears in the above-identified patent and that said Letters Patent is hereby corrected as shown below:

In Claims:

Col. 18
line 38, delete "timing" and substitute therefor --using--.

Signed and Sealed this

Fifth Day of September, 2006

JON W. DUDAS
*Director of the United States Patent and Trademark Office*